US010058482B2

(12) United States Patent
Haindl et al.

(10) Patent No.: US 10,058,482 B2
(45) Date of Patent: Aug. 28, 2018

(54) TRANSFER DEVICE FOR TAPPING OR DELIVERING A FLUID

(71) Applicant: Medac Gesellschaft fur klinische Spezialpraparate mbH, Wedel (DE)

(72) Inventors: Hans Haindl, Wennigsen (DE); Peter Henninger, Brachttal (DE); German Hamm, Cape Town (ZA)

(73) Assignee: MEDAC GESELLSCHAFT FUR KLINISCHE SPEZIALPRAPARATE MBH, Wedel (DE)

( * ) Notice: Subject to any disclaimer, the term of this patent is extended or adjusted under 35 U.S.C. 154(b) by 613 days.

(21) Appl. No.: 14/432,809

(22) PCT Filed: Sep. 30, 2013

(86) PCT No.: PCT/EP2013/070320
§ 371 (c)(1),
(2) Date: Apr. 14, 2015

(87) PCT Pub. No.: WO2014/053430
PCT Pub. Date: Apr. 10, 2014

(65) Prior Publication Data

US 2015/0209232 A1 Jul. 30, 2015

(30) Foreign Application Priority Data

Oct. 1, 2012 (DE) ........................ 10 2012 109 322
Dec. 21, 2012 (DE) ........................ 10 2012 113 002

(51) Int. Cl.
*A61M 5/32* (2006.01)
*A61J 1/20* (2006.01)
*A61J 1/14* (2006.01)

(52) U.S. Cl.
CPC ........... *A61J 1/2051* (2015.05); *A61J 1/1406* (2013.01); *A61J 1/20* (2013.01); *A61J 1/201* (2015.05); *A61J 1/2055* (2015.05)

(58) Field of Classification Search
CPC ........ A61J 1/2051; A61J 1/201; A61J 1/1406; A61J 1/20
See application file for complete search history.

(56) References Cited

U.S. PATENT DOCUMENTS 7,452,348 B2 * 11/2008 Hasegawa ............. A61J 1/2096
604/411
2014/0148777 A1 * 5/2014 Olesen .................. A61J 1/2096
604/414
2015/0209232 A1 7/2015 Haindl

FOREIGN PATENT DOCUMENTS

DE 698 08 432 T2 12/2003
DE 10 2005 006 771 A1 8/2006
(Continued)

OTHER PUBLICATIONS

International Search Report dated Jan. 13, 2014, corresponding to International Patent Application No. PCT/EP2013/070320.
Espacenet English abstract of DE 10 2005 006 771 A1.

*Primary Examiner* — Ariana Zimbouski
(74) *Attorney, Agent, or Firm* — Ladas & Parry LLP; Malcolm J. MacDonald

(57) ABSTRACT

The invention relates to a transfer device for tapping or delivering a fluid from a bottle sealed with a closure, the device having a hollow cylinder-shaped first part having a circumferential wall, which first part can be placed on the bottle and surrounds the closure, a hollow cylinder-shaped second part which can be adjusted with respect to the first part, the second part having a first wall running transverse to the longitudinal axis direction, and a puncturing needle originating from the first wall and extending in the direction
(Continued)

Figure 1:
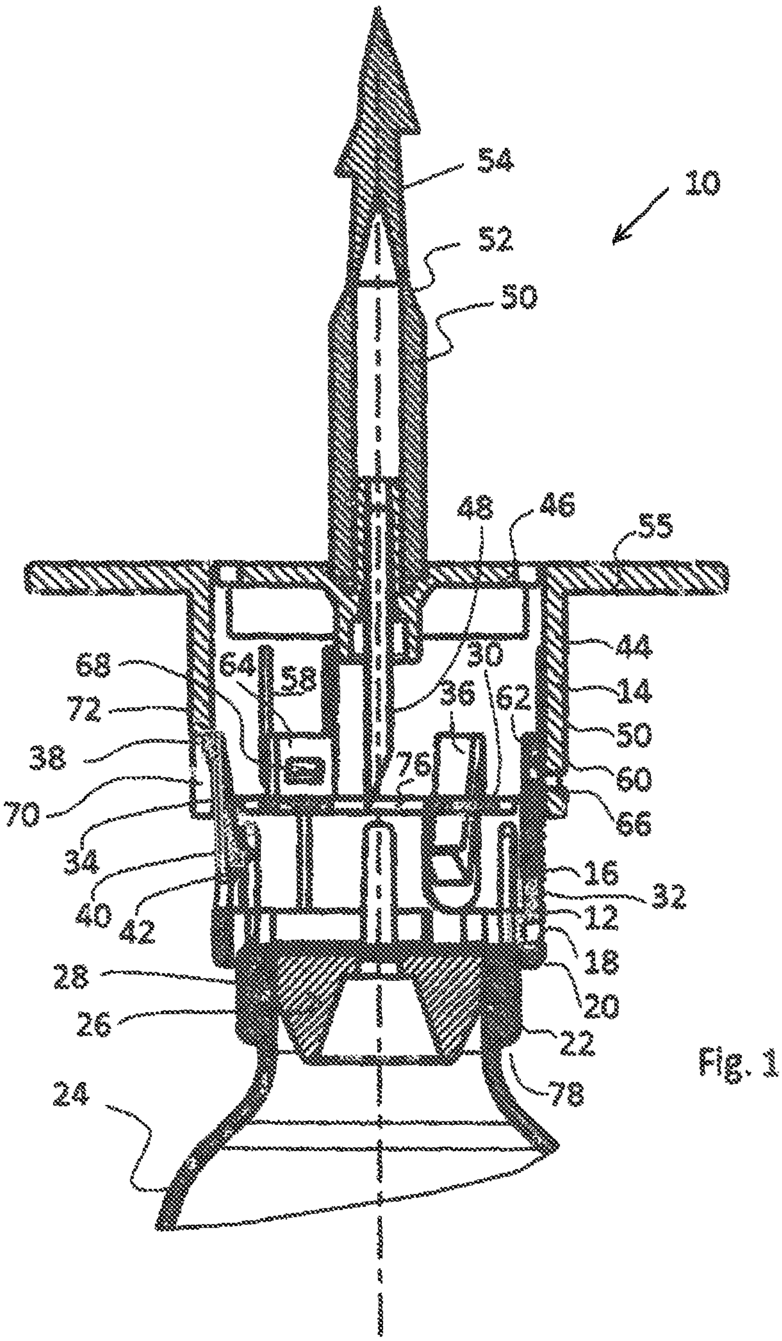

of the first part permitting piercing of the closure, wherein the first part cannot be adjusted axially with respect to the second part if the closure is not surrounded and, if the first part surrounds the closure, the first part can be adjusted with respect to the second part for piercing the closure.

20 Claims, 20 Drawing Sheets

(56) References Cited

FOREIGN PATENT DOCUMENTS

| | | | |
|---|---|---|---|
| DE | 10 2012 113 002 | A1 | 4/2014 |
| EP | 0311787 | A2 | 4/1989 |
| EP | 1574200 | A1 | 9/2005 |
| EP | 1430864 | B1 | 11/2010 |
| WO | 98/32411 | A1 | 7/1998 |
| WO | 0047159 | A1 | 8/2000 |
| WO | 2009/029390 | A1 | 3/2009 |
| WO | 2011140596 | A1 | 11/2011 |

* cited by examiner

TRANSFER DEVICE FOR TAPPING OR DELIVERING A FLUID

This application is a 371 of PCT/EP2013/070320, filed on Sep. 30, 2013, which claims priority to German Application No. 102012109322.9 filed Oct. 1, 2012, and German Application No. 102012113002.7 filed Dec. 21, 2012.

The invention relates to a transfer device for tapping or delivering a fluid from a bottle closed by a closure, comprising

- a hollow cylindrical first part that can be set on the bottle, surrounds the closure and comprises a circumferential wall,
- a hollow cylindrical second part that can be adjusted relative to the first part and with a first wall running transversely to the longitudinal axial direction,
- a puncturing needle starting from the first wall and extending in the direction of the first part for making it possible to pierce the closure, wherein if there is no surrounding of the closure (state before use) the first part cannot be axially adjusted axially or substantially cannot be axially adjusted relative to the second part and in the case of the first part surrounding the closure the first part can be adjusted relative to the second part for piercing the closure.

Numerous medications for infusion and injection are supplied as dry substances and are mixed to a solution or suspension only shortly before use/administration with water or some other solvent. The dry substance is supplied as a rule in an injection bottle, a so-called vial. Even primarily liquid medications are offered in vials. In order to connect this bottle to another container or to an infusion device a connector (transfer device) is required into which the head of the vial is pressed in and the vial membrane is perforated. The other container can be another injection bottle, an infusion bag or a hypodermic needle.

According to the prior art these connectors, that are also designated as adapters, can comprise a steel cannula or a plastic punch in the center that is surrounded by a collar forming a hollow cylindrical body, which collar snaps onto the flange-shaped edge with a vial flange cap consisting in particular of aluminum. The puncturing needle in particular in the shape of the steel cannula originates from the bottom wall of the collar and extends in the longitudinal direction of the hollow cylindrical body.

Such adapters no longer correspond to the current requirements for vial adapters for two reasons. On the one hand such products are required to be secure against causing injury by the accident protection regulation TRBA 250 and by a European guide line corresponding to it. If such vial adapters are provided with a steel cannula, they are not secure against causing injury since the diameter of the hollow cylindrical adapter, that is, the collar, is large enough for a finger to penetrate into it and therefore there is the danger of an injury caused by the cannula.

The second reason is that the plug of the puncturing needle must be punctured centrally in order to ensure a leak-proof connection of the vial. However, there is the danger in the vial adapters used according to the prior art that the vial is tilted when being snapped into the collar. This causes a primarily eccentric puncturing of the plug. During the subsequent complete pressing in of the vial the cannula is then forced into the central position. As a result, the vial plug is placed under tension that can lead to leakage adjacent to the cannula. In the case of toxic substances such as, e.g., cytostatic agents this can result in the endangering of personnel and patients.

A transfer device of the initially cited type can be gathered from EP 1 430 864 B1. The transfer device consists of a cap-like outer guide part and a tubular inner guide part that can be telescopically shifted together. In the unused state the beginnings of the inner guide part engage in recesses of the outer guide part that run on the inside. If the transfer device is pushed onto a vial, tongue-like elements originating from the inner guide part are bent outward with the result that the outer guide part is adjusted outward in the area of the recesses so that the engagement between the inner and the outer guide part is canceled. Independently of this, the puncturing needle that originates from the outer guide part is freely accessible in the delivery state via the opening of the inner guide part so that there is the same danger of injury as in the case of transfer devices that are integrally constructed.

DE 10 2005 006 771 A1 teaches a transfer device comprising a needle holder with transfer needle which holder can be axially adjusted in a hollow cylindrical structure. The structure comprises a wall-shaped stop that can be set on to the opening of a storage container to be perforated and is perforated during the activation of the transfer device by the transfer needle.

A transfer device according to DE 698 08 432 T2 comprises an actuator in order to be able to axially adjust a first part comprising a pin to a second part surrounding a closure of a bottle.

The present invention has the basic task of making available a transfer device, that is, a vial connector or vial adapter that is in particular injury-proof. Also, according to another aspect it should be ensured that in the case of an unlocking of the adapter parts it is no longer possible to pull the first part off the second part or to pull the second part out of the first part. If necessary, the possibility should also be created that during the puncturing of the closure of the vial a leakage of fluid parts or aerosols from the vial is prevented.

The invention solves the task substantially in that the first part comprises a second wall running transversely to the longitudinal axis of the first part and that if the first and the second part cannot be axially adjusted or cannot be substantially axially adjusted relative to one another the distal end of the puncturing needle runs between the first and the second wall. As a result of the fact that the inner or first part comprises an intermediate or bottom wall designated as the second wall in its area remote from the opening and when the first and second part are engaged, the of the puncturing needle is surrounded by the intermediate wall of the first part and on the circumferential side by the circumferential wall of the second part, it is ensured that the danger of injury is extruded even if a finger moves into the inner space of the first part.

In order that during the adjustment of the first part to the second part the perforating of the closure, that is basically a membrane in accordance with the prior art consisting of aluminum and flanged around the flanged-like edge of the vial, is not adversely affected, it is provided that the second wall is perforated in the axial extension of the puncturing needle.

In order to ensure with constructively simple measures that if no vial has been set yet into the transfer device there is no adjustability or substantially no adjustability between the first part and the second part, and even then if relatively large axial forces are acting on the transfer device, the invention provides that one or more preferably tongue-like lever elements originate from the circumferential wall of the first part which elements have the first section extending in a direction of the second part and a second section extending in the direction of the opening of the first part running on the bottom side, whereby given the lack of axial adjustability or substantial lack of axial adjustability between the first and the second part relative to one another the first sections project laterally outward over the circumferential wall of the first part and the second sections extend to the inside of the first part, the first sections interact with the second part in order to prevent a shifting of the first part into the second part, and when the first part surrounds the closure of the bottle and in particular locks it, the second sections of the lever elements are adjusted radially outward with simultaneous moving into engagement of the first sections with the second part.

Tongue-like lever elements that originate from the first part are used to prevent an adjustability of the first to the second part in as far as a vial was not set into the first part and the first part is locked with the flange-like edge of the vial. Since the lever elements extend in the longitudinal direction of the transfer device, that is, of the connector, they can absorb great forces without the risk of an uncontrolled pivoting taking place. If the transfer device is pushed onto a vial, the second or inner sections of the lever elements slide along the circumferential surface of the closure and are radially pivoted outward with the consequence that the first or outer sections of the lever elements are pivoted radially inward and therefore move into engagement with the second part holding the puncturing needle. There is then the possibility that the required relative position between the first and the second part takes place and therefore the puncturing needle can perforate the closure. At the same time an exact axial guidance is given that ensure a central perforating of the closure since the first part is axially guided to the second part.

In order to make possible the axial adjustment of the first part, that is, the bottle container or vial container, to the second part, that is, the puncturing needle holder or cannula holder, a telescopic shifting of the parts to one another or a rotation of these parts to one another can be performed. During the rotation an axial adjustment of the first to the second part also takes place in order to adjust the puncturing needle in the direction of the vial and in order to penetrate its closure.

In order to exclude the loosening of the first from the second part, it is provided in particular that the first part and the second part are locked to one another during the axial lack of adjustability or substantial lack of axial adjustability whereby projections originating preferably from the inside of the circumferential wall of the second part engage in recesses of the circumferential wall of the first part.

According to another embodiment of the invention that is also to be emphasized it is furthermore provided that the first part can basically be adjusted to the second part exclusively in the direction of penetration, and therefore a withdrawal is not possible. To this end it is provided in particular that the circumferential wall of the first part comprises recesses spaced in the axial direction from each other for the gradual locking of the projections. As a result, a type of engagement is made available that allows a ready pushing in of the first part into the second part, that is, of the inner part into the outer part, but prevents a withdrawal.

Other technical solutions that also ensure that the first part can be adjusted in the direction of the vial without allowing a withdrawal are also comprised by the invention.

In other words, the invention is also distinguished by a transfer device for the tapping or delivering of a fluid from a bottle closed by a closure, comprising a first hollow cylindrical part that can be set on the bottle, surrounds the closure and has a circumferential wall, comprises a hollow cylindrical second part that can be adjusted to the first part and comprises a first wall running transversely to the longitudinal axial direction, a puncturing needle running from the first wall and extending in the direction of the first part and making possible a puncturing of the closure, wherein the first part can interact with the second part during their adjustment to one another in the axial direction in such a manner that the second part can be exclusively or substantially exclusively adjusted in the direction of penetration to the first part and consequently a withdrawal is prevented.

The solution in this regard can of course also be combined with other features of the transfer device.

In order to make possible a guided rotation of the first part to the second part for their axial adjustability the invention provides in particular that a helically running contour like a projection running in a strip is formed in one of the parts along its circumferential wall and around the longitudinal axis of the part with which contour an element such as a tongue originating from the other part, in particular from its circumferential wall, interacts. The contour can have a serrated profile and the element can comprise a projection such as a hook that interacts with the contour, wherein an interaction takes place in such a manner that an unimpeded rotation of the first part to the second part takes place exclusively in the direction of penetration of the puncturing needle. This measure ensures that an axial adjustment of the first part into the second part, that is, of the vial holder into the cannula holder is possible, that is, the puncturing needle is adjusted in the direction of the vial but not inversely.

In particular, it is provided that the contour projects over the outer circumferential surface of the first part, that the inner circumferential surface of the second part comprises at least one recess adapted to the course of the contour at least in sections in which recess the contour is guided. Therefore, it is ensured even in the case of a small length of the connector that an unobjectionable axial adjustment to one another is possible.

In order to ensure during the rotation of the cannula holder, that is, of the second part, that the first part, that is, the vial holder, does not rotate with it, it is furthermore provided that a handle projects from the first part, in particular two wings running diametrically toward one another and projecting from the first part, by means of which the first part can be fixed on the bottle, that is, the vial.

The invention furthermore provides that the second part comprises tongue-shaped elements limited by slots running in the longitudinal direction of the second part and with projections projecting into the interior of the second part, that the projections engage into recesses in the first part upon the lack of axial adjustability or the substantial lack of axial adjustability between the first part and the second part which recesses have a distance to the lower edge of the first part such that given a locked surrounding of the bottle by the first part the projections interact with the bottle or an element originating from it for moving into engagement with the recesses. It is provided here in particular that the projections are constructed like ramps or wedges at their free ends in such a manner that that a surface running obliquely to the longitudinal direction slides along the bottle or its edge.

The invention furthermore provides that the opening-side edge of the first part comprises inwardly projecting projections for extending behind a flange-like edge surrounding the opening of the bottle, wherein an unlocking does not take place between the first sections of the lever elements and the second part before the extending behind the flange-like edge. As a result of the extension behind, the first part snaps onto the vial, that is, its edge constructed like a flange.

The intermediate wall that quasi-protects the tip of the puncturing needle when the transfer device is not being used is brought to rest on the first part of the outside of the closure during the insertion of the first part into the second part or the pushing of the second part onto the first part so that the required transfer of force is made possible in order to move the first part to the second part.

In order to ensure that no aerosols can be released in the case of toxic substances during a puncturing of the closure, a further embodiment of the invention provides that an element such as a membrane or a plug running in the axial extension of the puncturing needle and sealing the puncturing needle on the circumference side during the perforation originates from the second wall. The corresponding elements consist in particular of elastomeric material that is punctured by the puncturing needle and at the same time is pressed against the closure of the vial. The corresponding elements such as a membrane or a plug then seal the puncturing needle on the circumferential side. At the same time a sealing against the outside of the closure takes place. This ensures that during the puncturing of the structural components the contents of the vial cannot pass into the environment.

According to the invention in a bipartite connector is made available, whereby the parts are arranged telescopically against one another and can be adjusted toward one another. The inner or the first part comprises barbs for the snapping in of the vial head and the outer or the second part comprises the puncturing needle for perforating the vial closure. In the supplied state of the vial the inner part extends out of the outer part, wherein the cannula tip lies protected behind the wall of the inner or first part, which wall is to be designated as a bottom. Therefore, if a user unintentionally reaches into the interior of the connector or adapter, there is no injury from the tip of the puncturing needle. In order that the inner part cannot be pressed into the outer part before the connection with the vial already, lever-like blocking devices are provided on the circumference of the inner part that prevent the inner part from being able to be pushed into the outer part. The blocking levers are not pressed outward from the vial head until the vial head has been completely pushed into the inner part. They pivot here about an axis so that the end extending in the direction of the outer part and which otherwise blocks the pushing in of the inner part into the outer one is pivoted inward and therefore the path is freed for the adjustment such as the pushing in or rotating the inner part into the outer part of the vial adapter. When the inner part has been complete pushed in or pushed in to the required extent into the outer part a non-detachable locking with the outer part takes place. During this adjusting process such as a pushing in or rotary process the puncturing needle punctures the closure, that is, the membrane of the vial plug.

In order that it cannot occur that the inner part is half pushed in, the cannula already perforates the membrane and then the vial is again pulled back with the first part so that substances entered into the cannula might exit, it is provided in particular that a toothed engagement is attached on the outer side of the inner part which engagement allows an easy pushing in of the inner part into the outer part but no pulling back. Alternatively, this is ensured by the helically running contour with the serrated profile.

Since it can be important that in the case of toxic substances no aerosols are released during the puncturing of the membranes, elastomeric structural elements can be arranged on the inner wall of the inner part that are punctured by the puncturing needle and are pressed at the same time against the outside of the closure of the vial. These structural elements seal around the cannula as well as opposite the vial closure so that the substances from the vial cannot escape into the environment during the perforation.

All these previously explained measures have an inventive content.

Other details, advantages and features of the invention result not only from the claims, the features to be gathered from them by themselves and/or in combination but also from the following description of a preferred exemplary embodiment to be gathered from the drawings.

Figure 2:
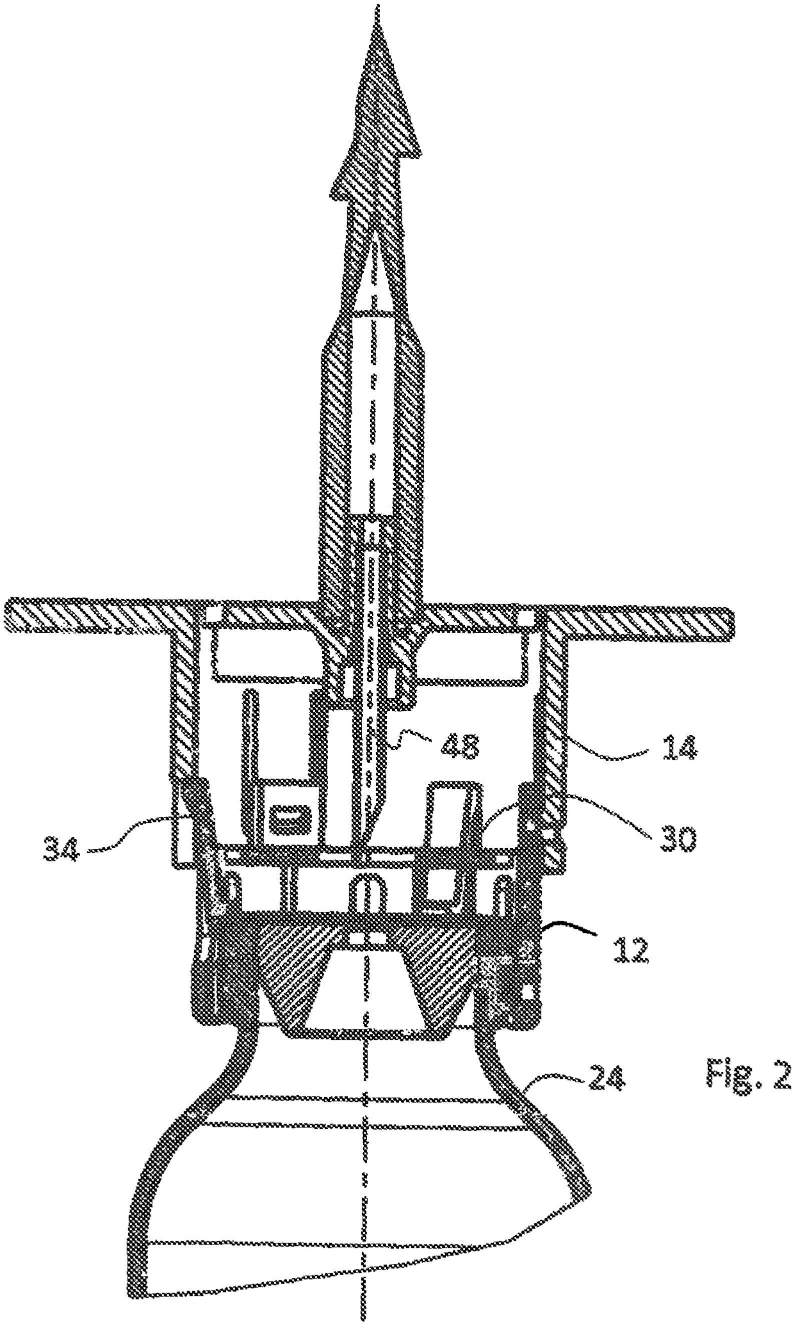
Figure 3:
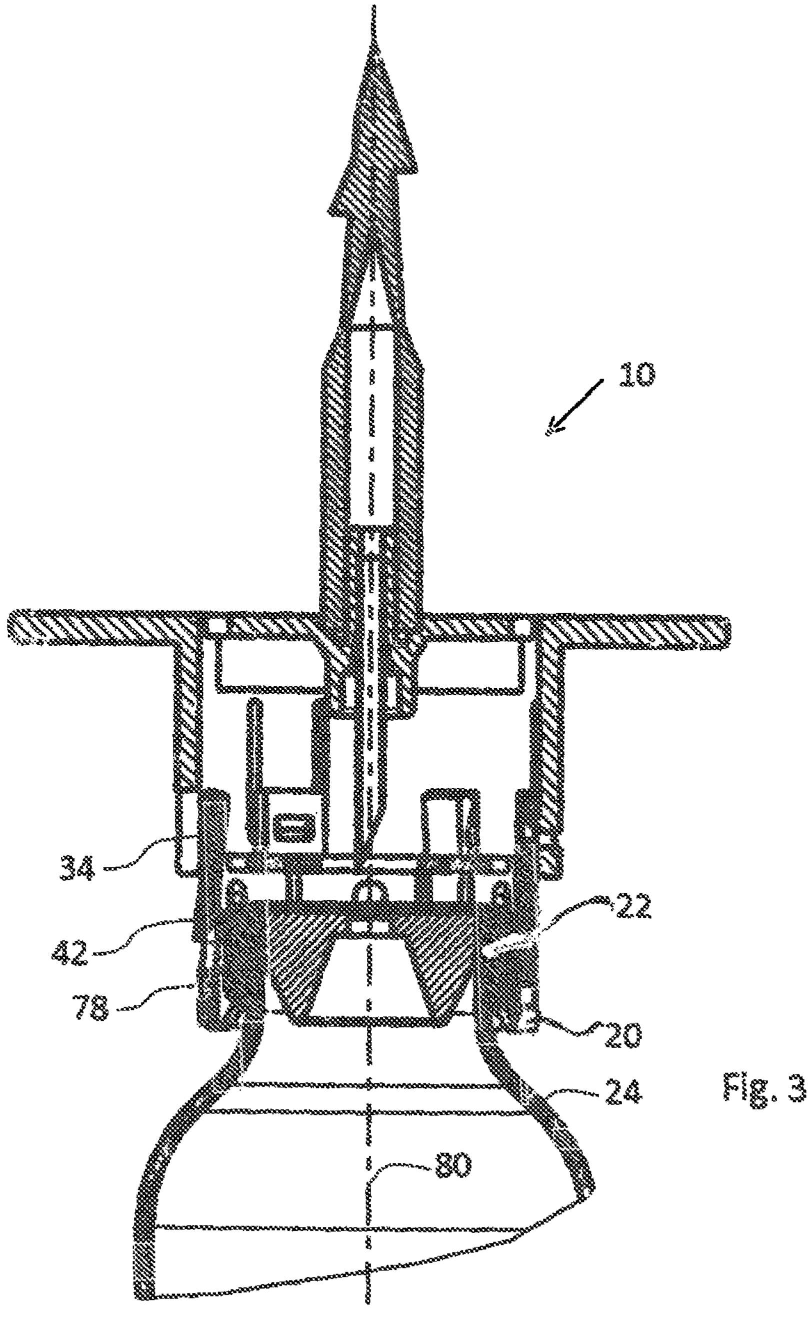
Figure 4:
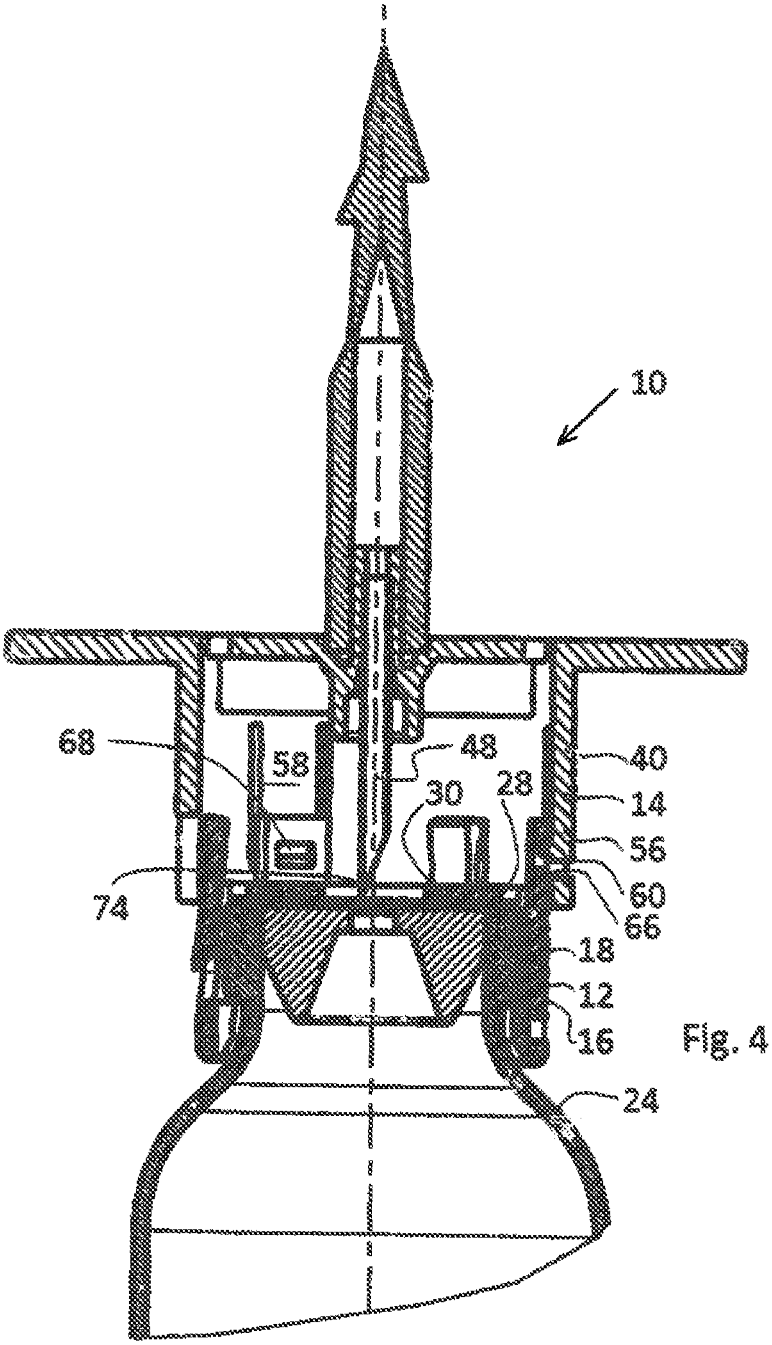
Figure 5:
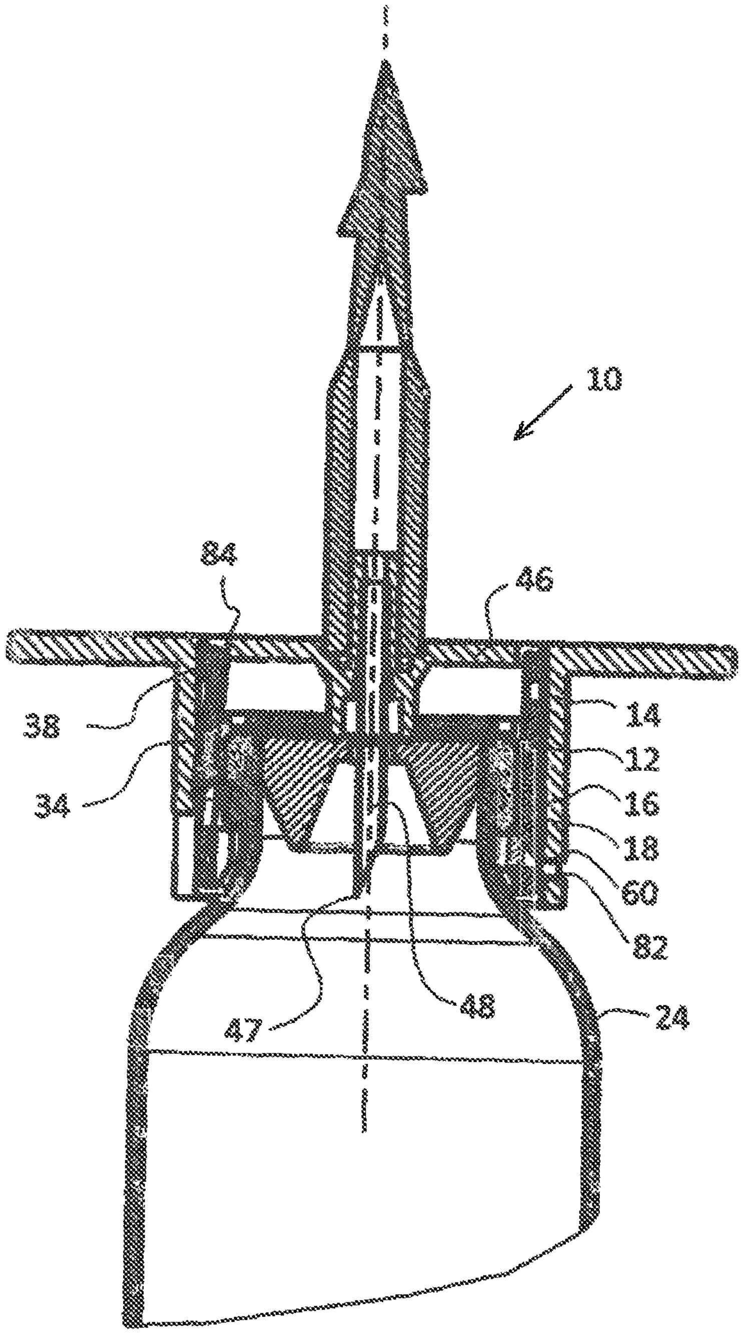
Figure 6:
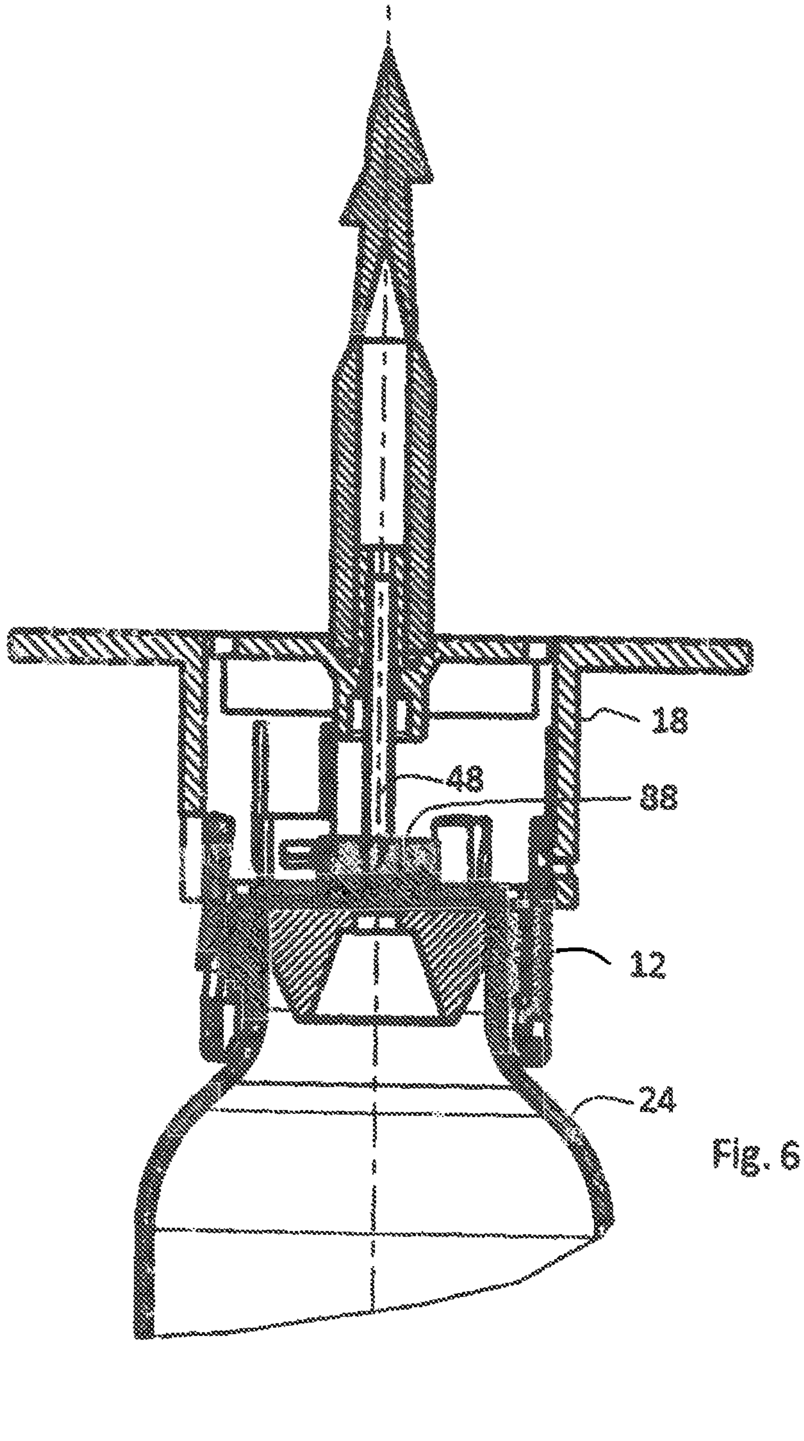
Figure 7:
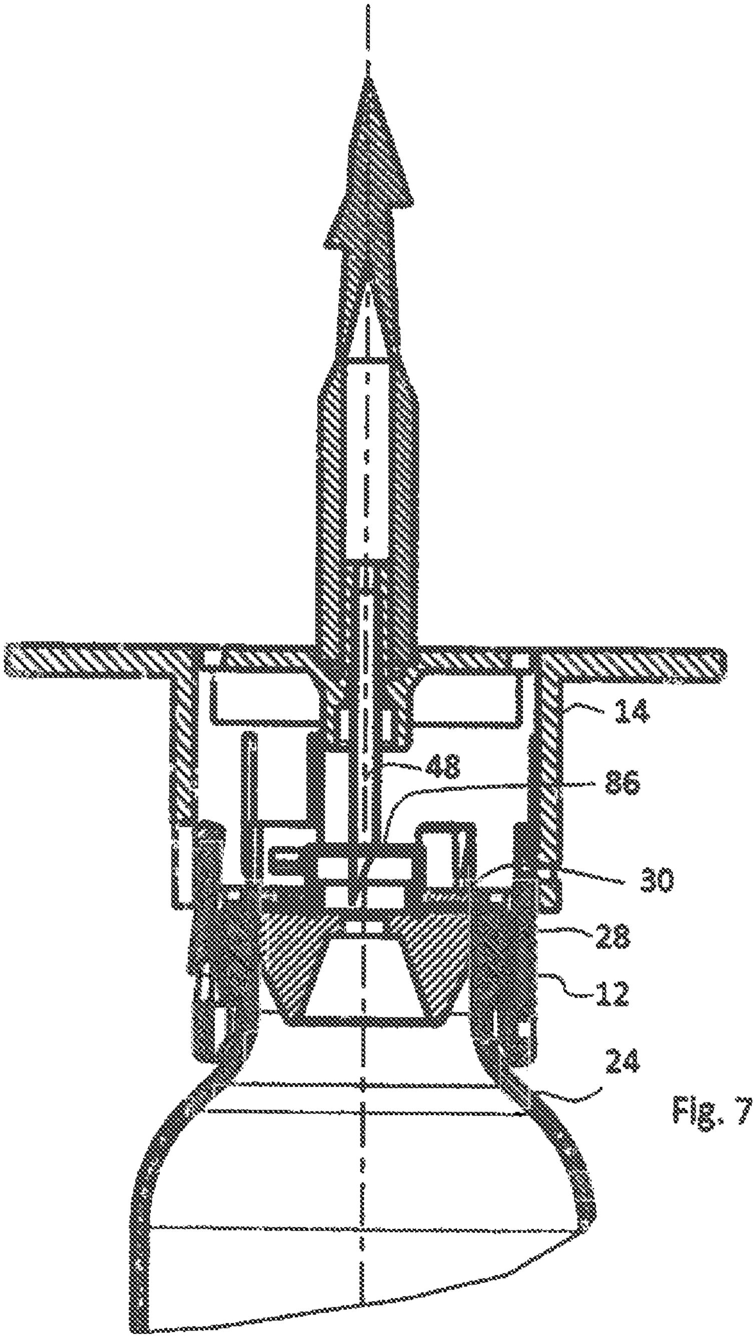
Figure 8:
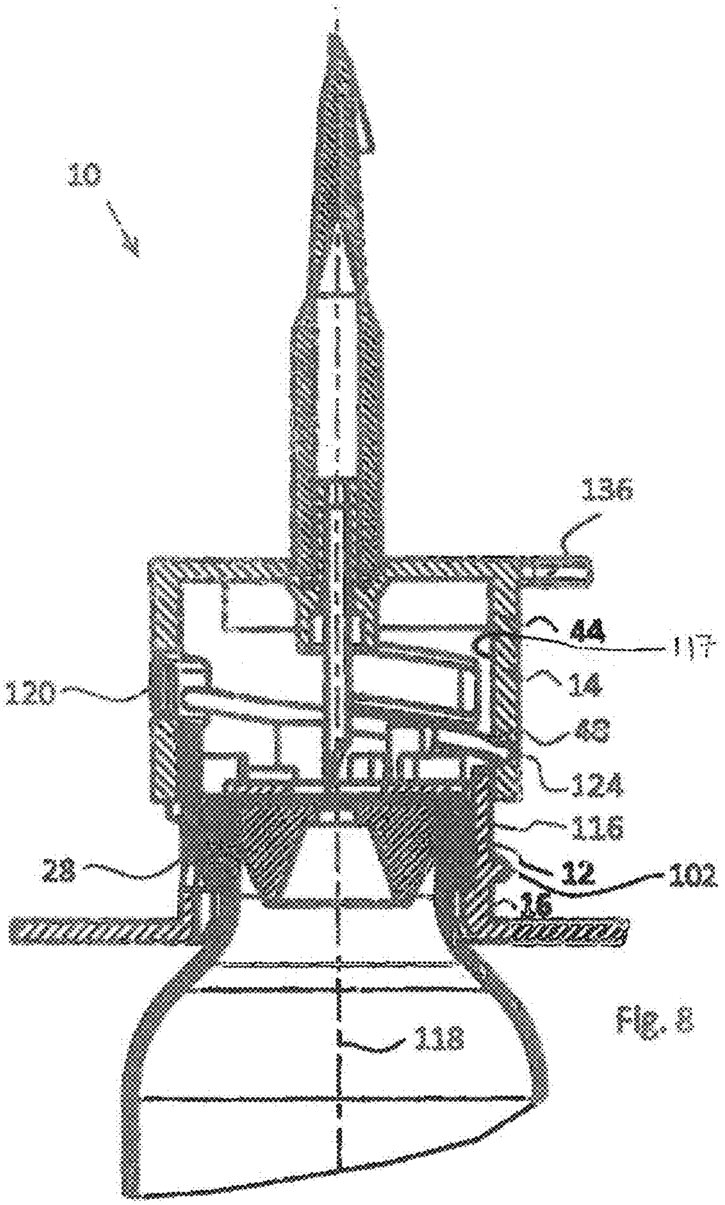
Figure 9:
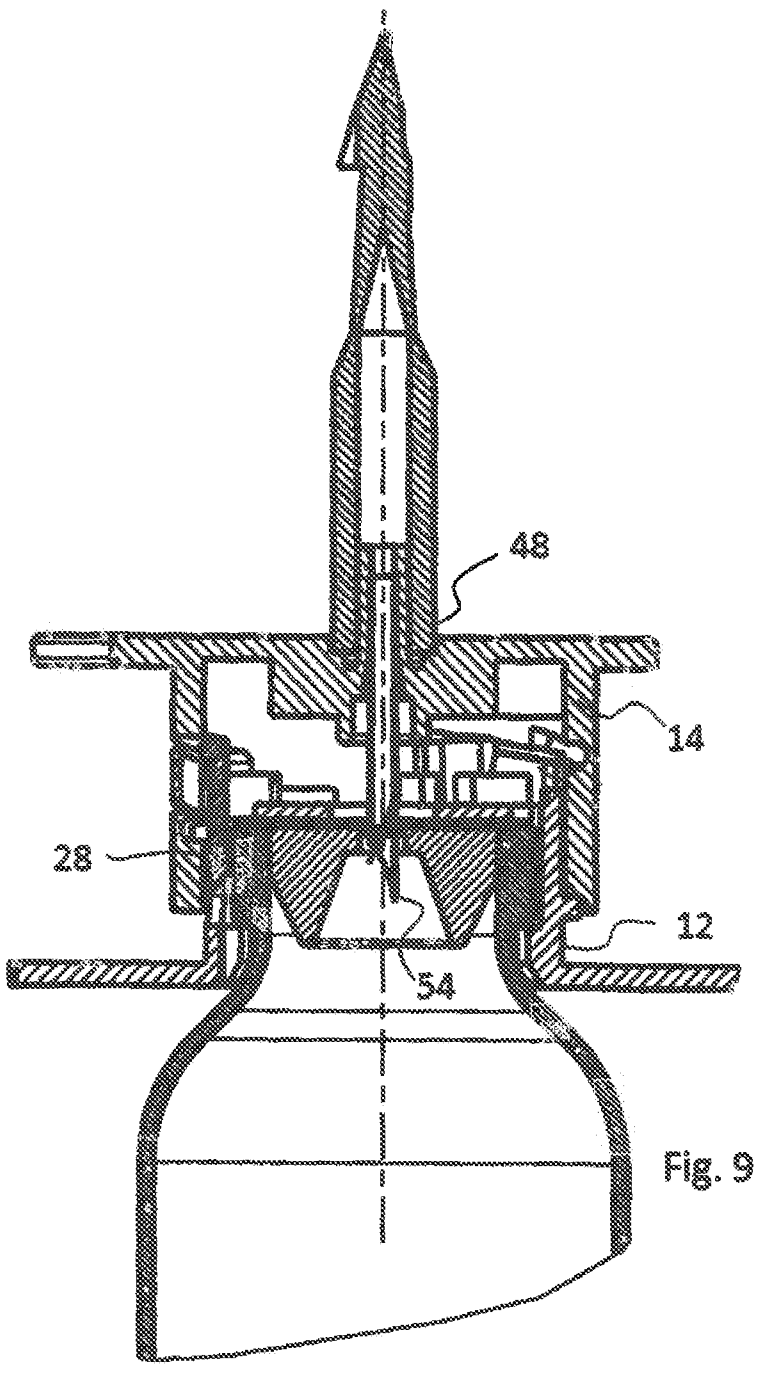
Figure 10:
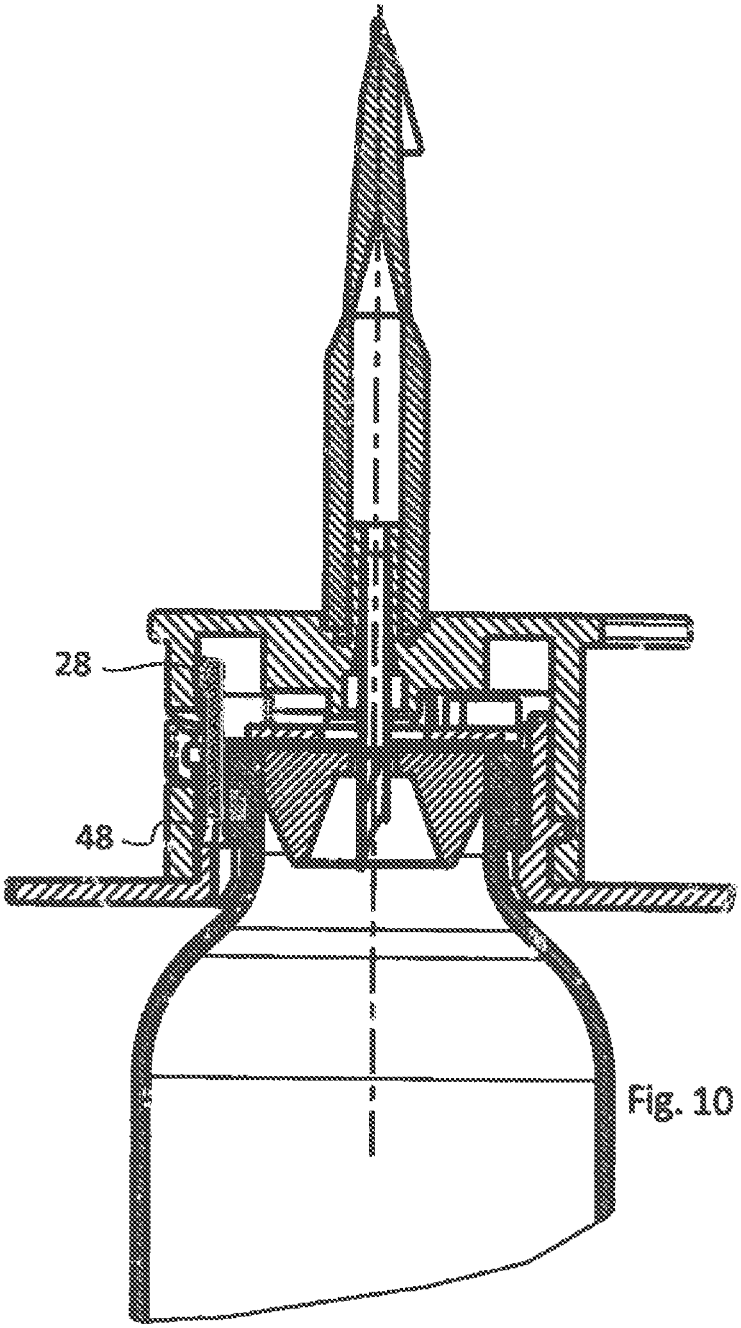
Figure 11:
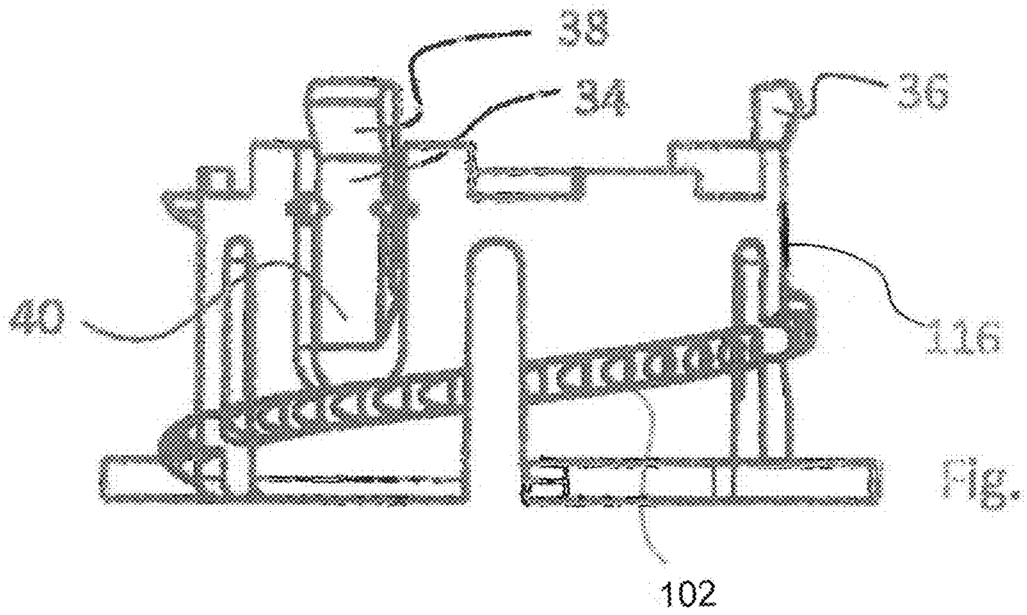
Figure 12:
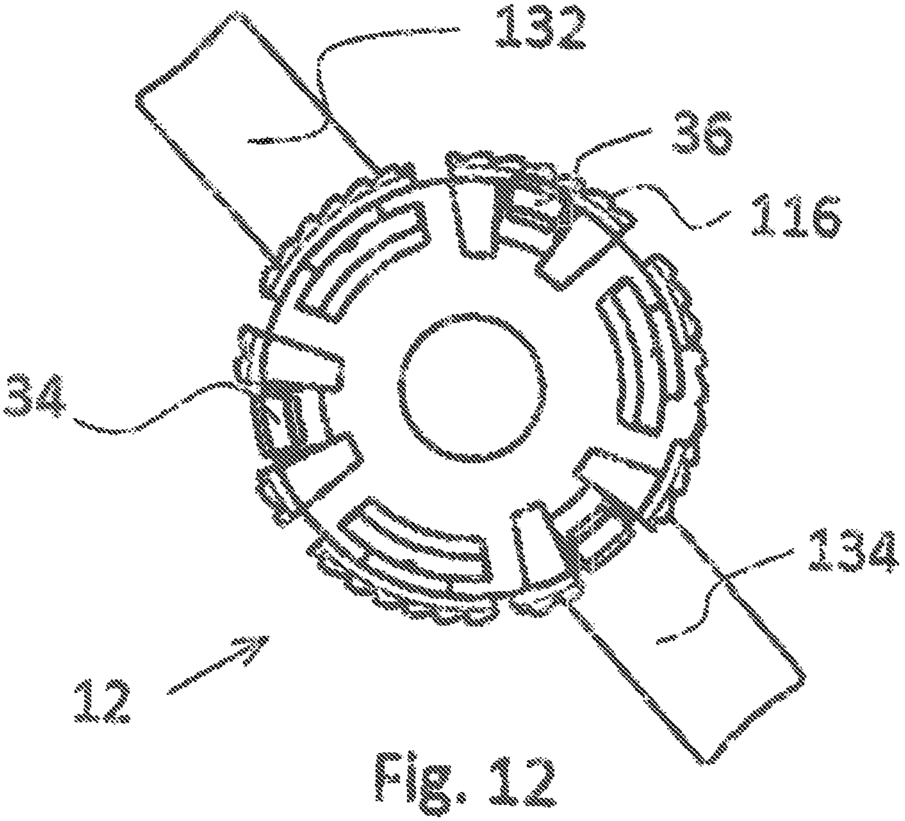
Figure 13:
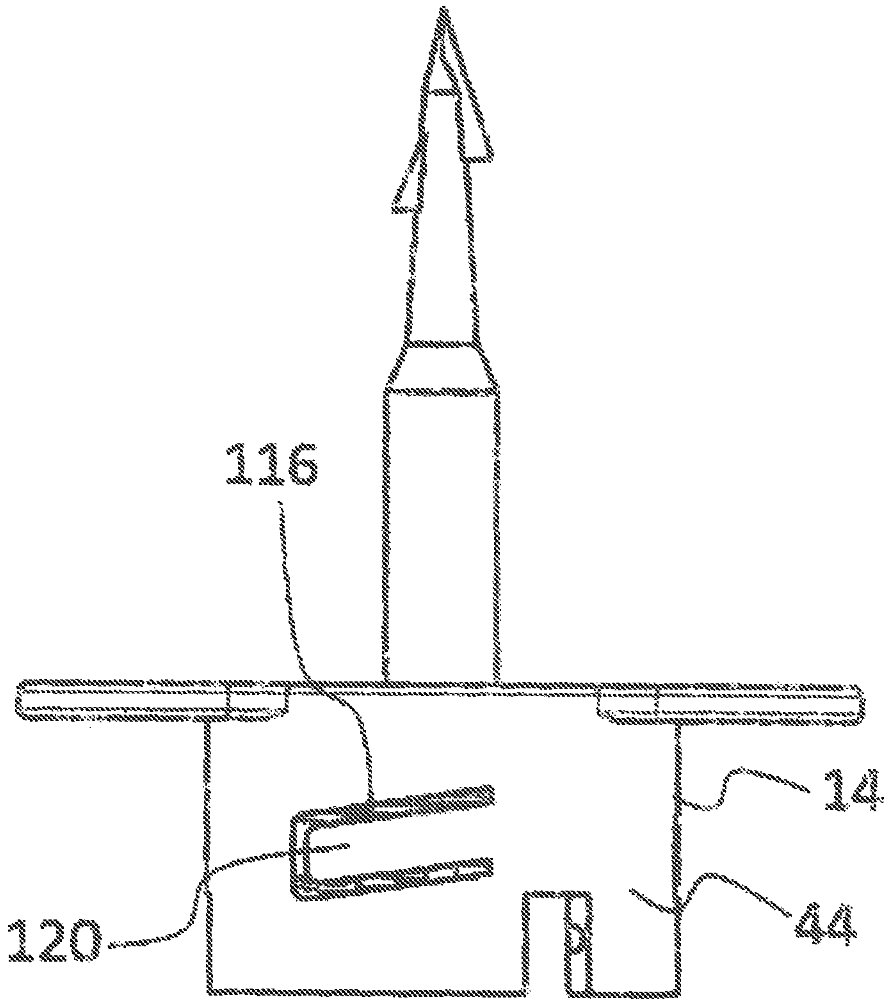
Figure 14:
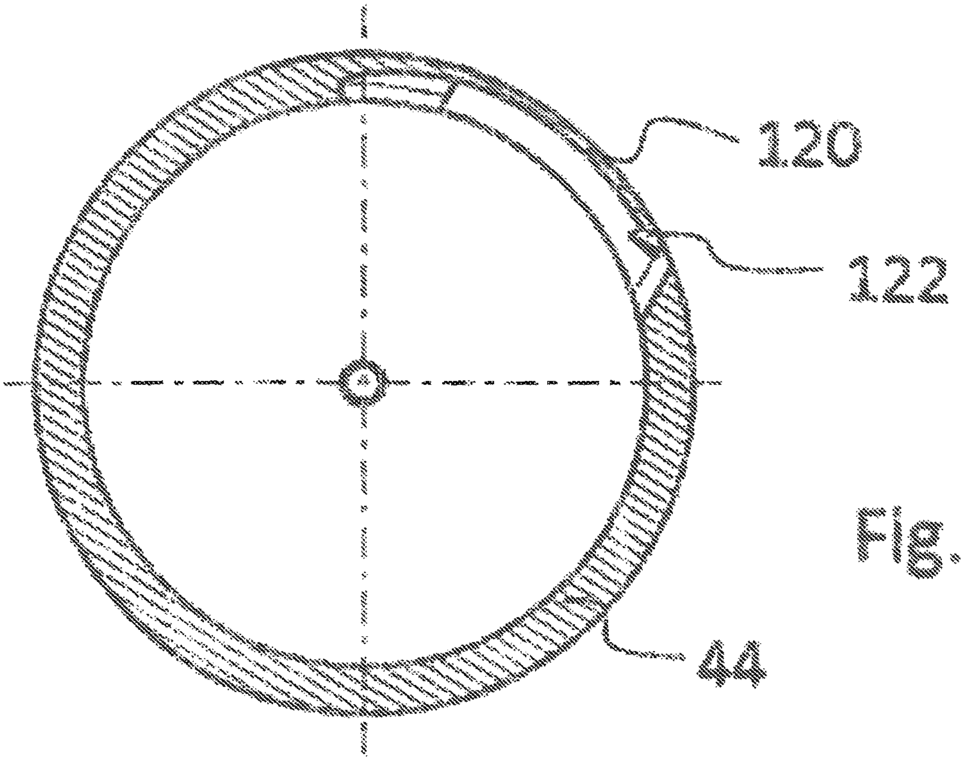
Figure 15:
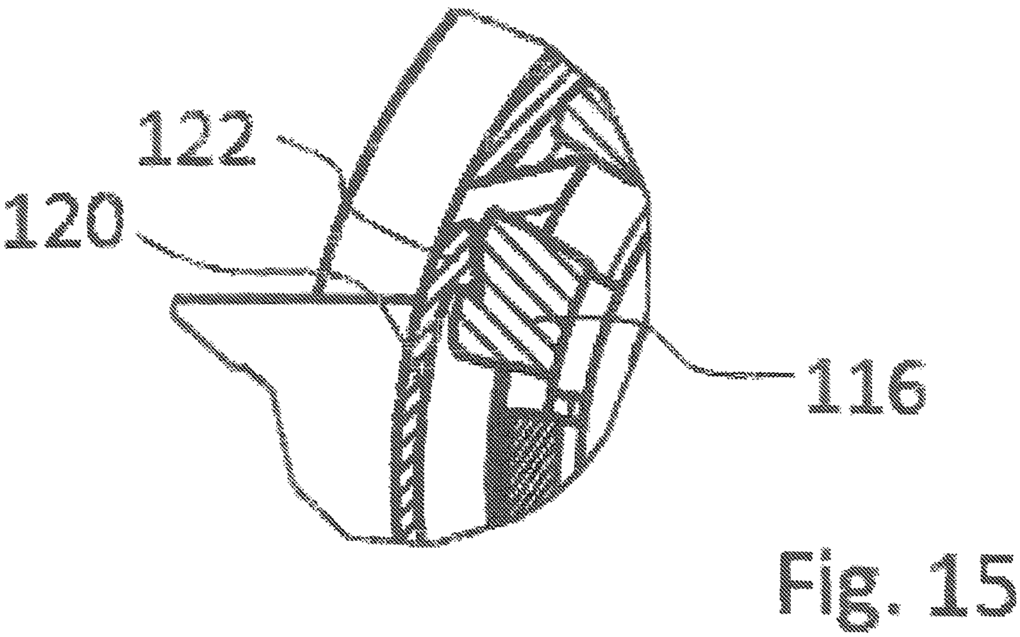
Figure 16:
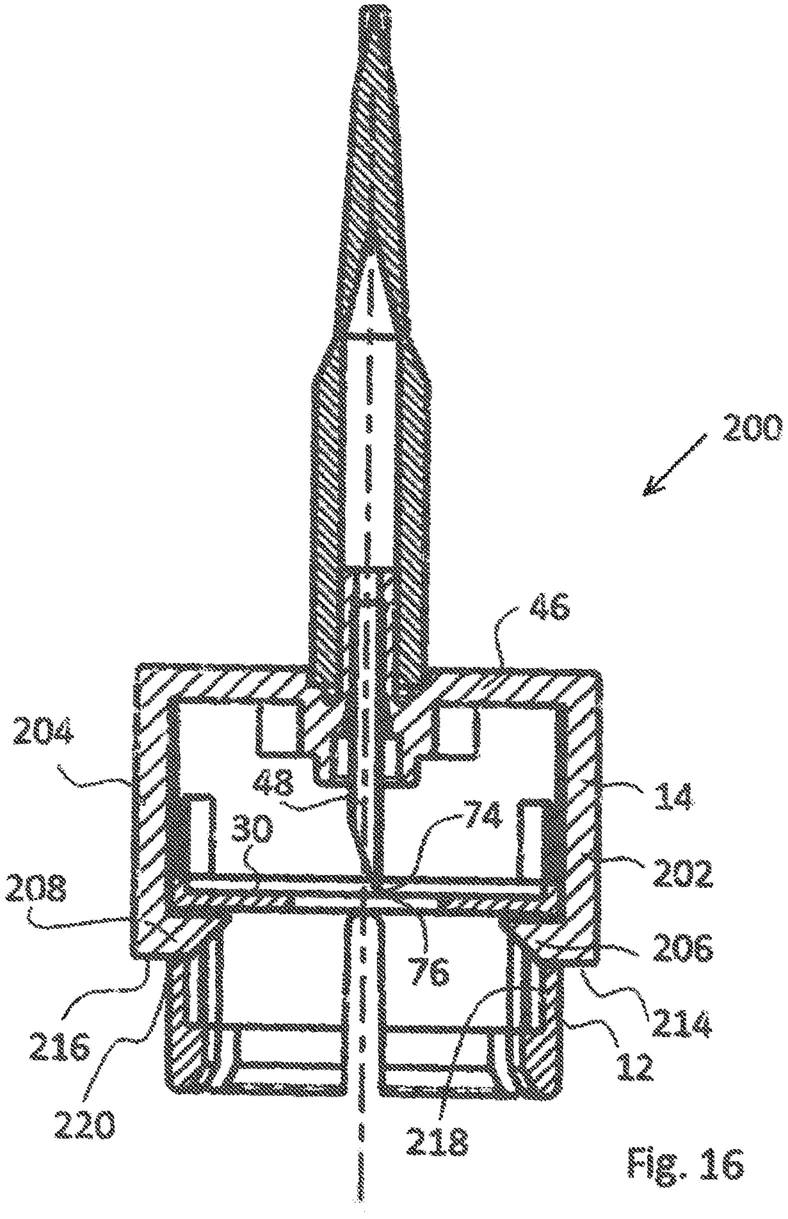
Figure 17:
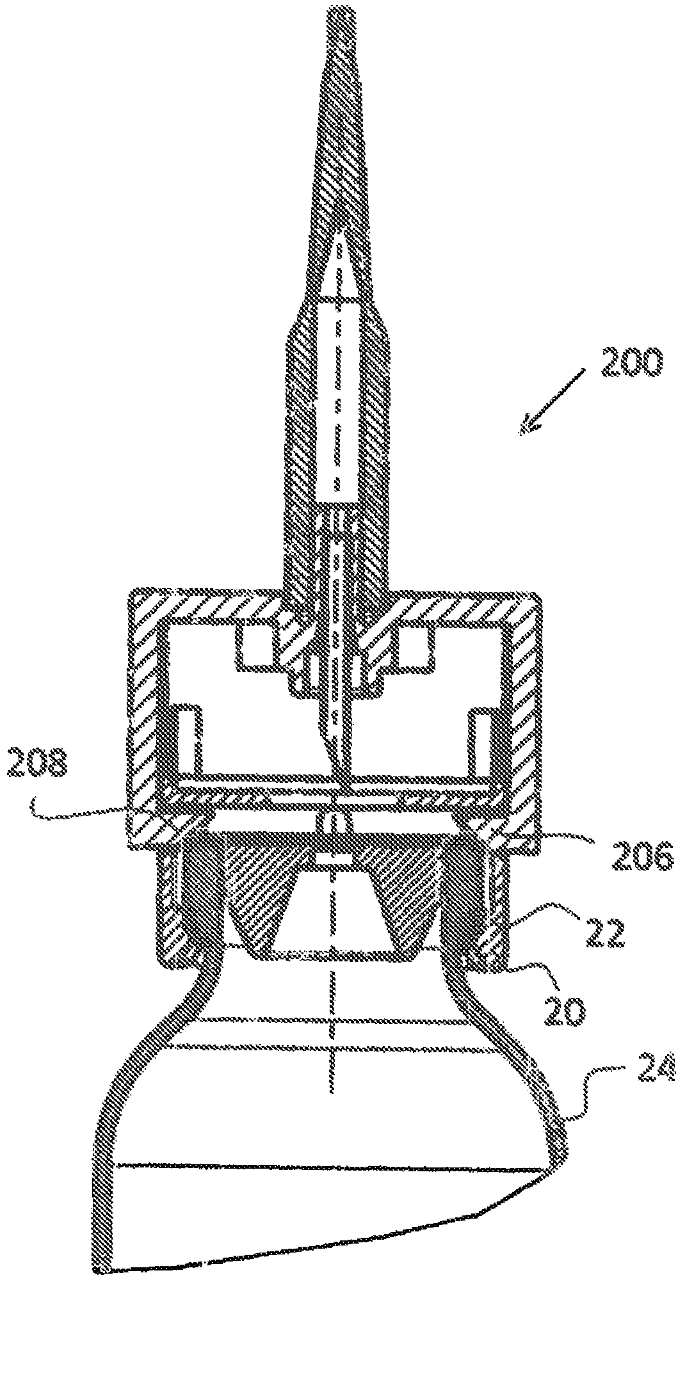
Figure 18:
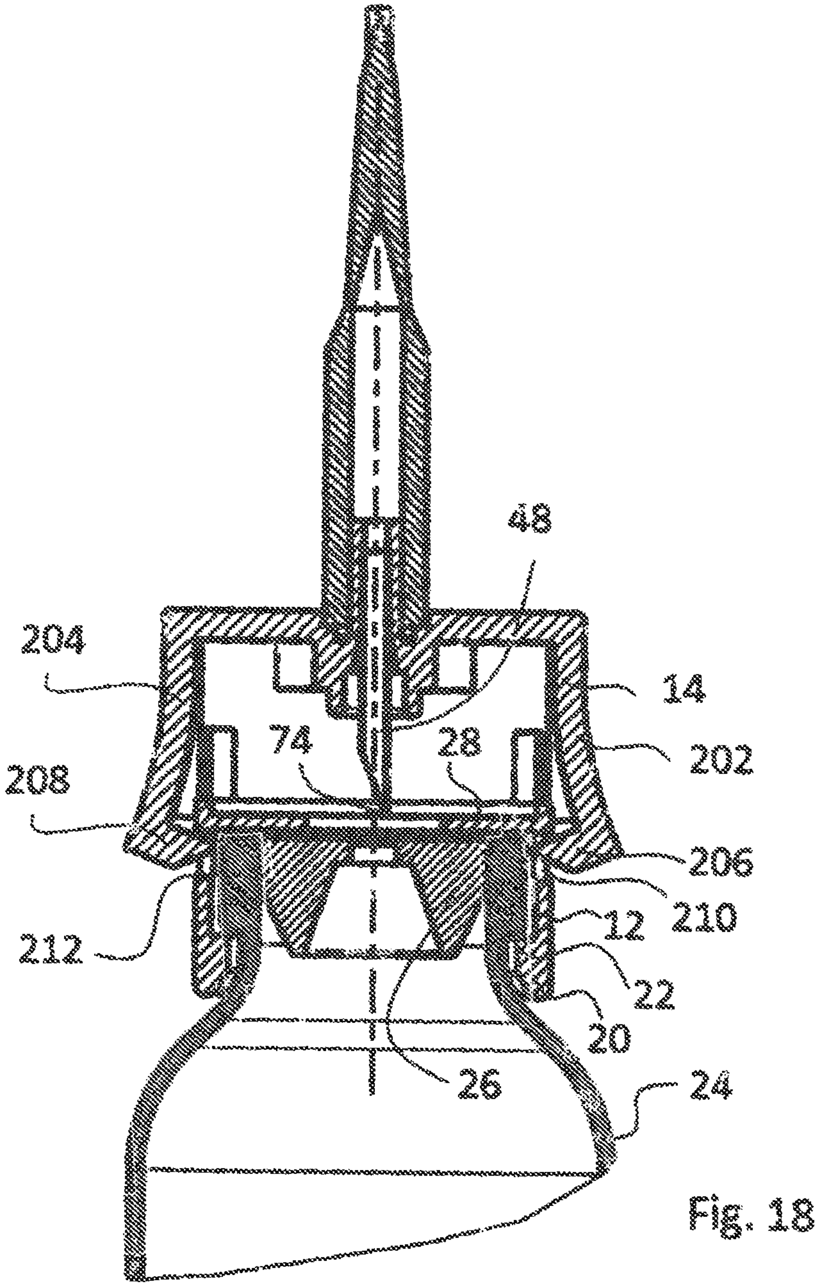
Figure 19:
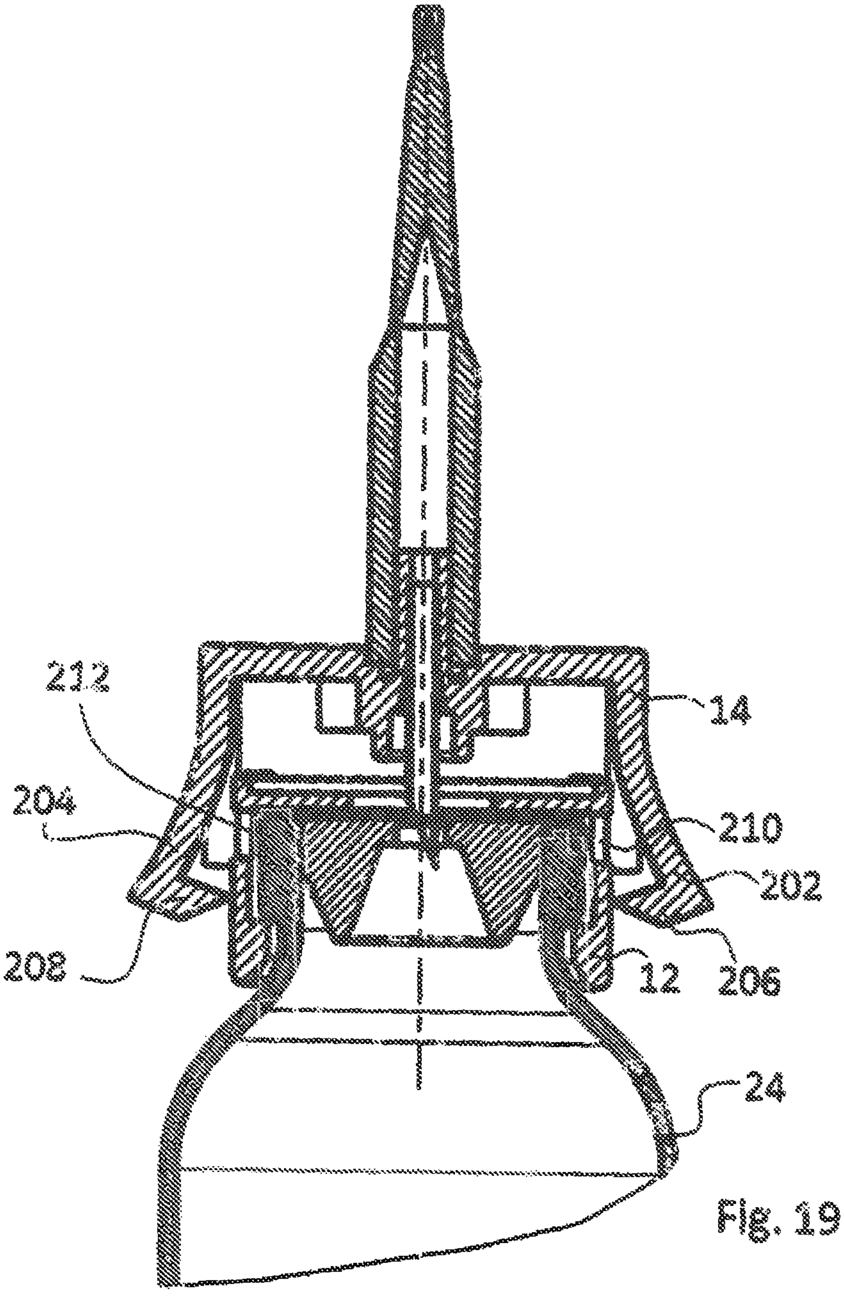
Figure 20:
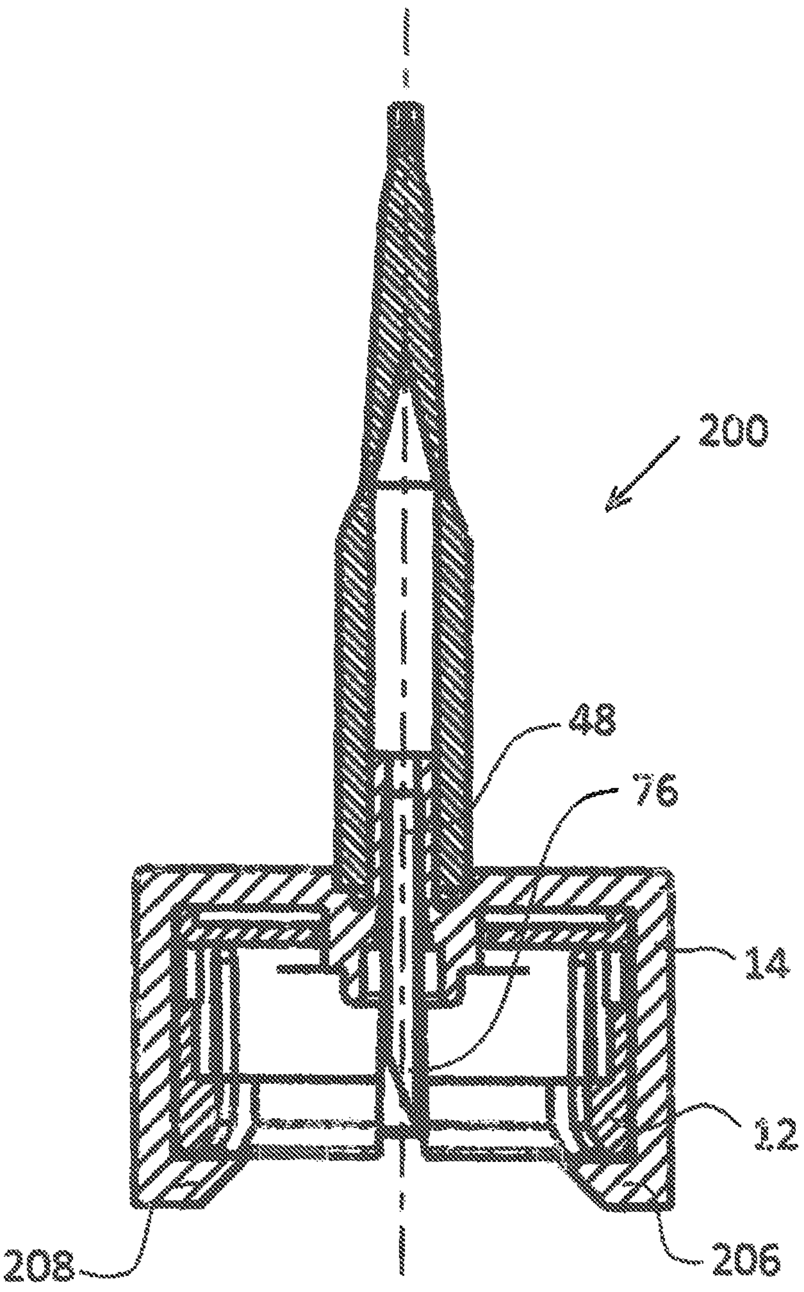

In the drawings:

FIG. 1 shows a first embodiment of a transfer device partial section in the locked state, FIG. 2 shows the transfer device according to FIG. 1 before the unlocking, FIG. 3 shows the transfer device according to the FIGS. 1 and 2 after the unlocking, FIG. 4 shows the transfer device according to the FIGS. 1 to 3 before the penetration, FIG. 5 shows a transfer device according to the FIGS. 1 to 4 in the final position, FIG. 6 shows a second embodiment of a transfer device, FIG. 7 shows a third embodiment of a transfer device, FIG. 8 shows a fourth embodiment of a transfer device for penetration of a closure, FIG. 9 shows a transfer device according to FIG. 8 during the penetration, FIG. 10 shows the transfer device according to FIGS. 8 and 9 at the end of the penetration, FIG. 11 shows a side view of first part of the transfer device according to FIGS. 8 to 10, FIG. 12 shows the first part according to FIG. 11 in a top view, FIG. 13 shows a side view of a second part of the transfer device according to FIGS. 8 to 10, FIG. 14 shows a section through the second part according to FIG. 14, FIG. 15 shows a section of the first and of the second part, FIG. 16 shows a sixth embodiment of a transfer device without bottle, FIG. 17 shows the transfer device according to FIG. 16 in a position partially pushed onto a bottle, FIG. 18 shows the transfer device according to the FIGS. 16 and 17 in an unlocked position, FIG. 19 shows the transfer device according to the FIGS. 16 to 18 after a partial penetration of the bottle closure, and FIG. 20 shows the transfer device according to the FIGS. 16 to 19 in their final position but without bottle.

The figures, in which basically the same elements are provided with the same reference numerals, show transfer devices by means of which fluids such as dry substances or liquids such as water or solvents that are mixed for purposes of infusion or injection before their use or administration from a bottle or a flask, a so-called vial, are transferred. Appropriate transfer devices are also designated as connectors or adapters. In order to connect the bottle to another container or to an infusion device an appropriate transfer device is required in order to perforate the closure of the flask by a puncturing needle—such as a steel cannula—in order to then be able to supply the fluid to be removed from the flask via the transfer device, e.g., to an injection bottle, an infusion bag or a hypodermic needle.

The transfer devices to be gathered from the figures comprise parts that are telescopically arranged into one another and can be adjusted relative to one another that are designated as the first part and the second part or the inner part or the outer part. For reasons of simplicity the transfer device is designated in the following as connector and the flask to be connected to it as vial. The first part is also designated as vial holder and the second part as cannula holder.

It should be noted regarding the indicated geometries of the structural components that they are to be understood purely by way of example and that modifications also possible to the extent that the basic principles of the invention can be realized. For the rest, the figures are self-explanatory. The features decisive for the invention can be clearly recognized in them.

The FIGS. 1 to 5 show a first embodiment of a connector 10 composed of an inner or first part 12 and a second or outer part 14 that are telescopically arranged relative to one another and can be axially shifted relative to one another. The inner part 12 and the outer part 14 are in particular an injection-molded part and consist of a suitable plastic.

The inner part 12 comprises a circumferential wall 16 with the shape of a hollow cylinder that comprises tongue-like and therefore movable sections that are limited on the circumferential side by slots and have projections 20 extending inward with their free ends in order to extend behind a flange-like edge 22 of a vial 24 in a position of use, as is shown in FIGS. 4 and 5. The flange-like edge 22 has an opening for the vial 24 that is closed by a closure plug 26.

After the closing of the vial 24 with the closure plug 26 an aluminum flange cap is typically placed on it. A flip-off cap of plastic can be present on the latter. This flip-off cap is drawn off from the aluminum flange cap so that a "hole" is created in the middle of the aluminum flange cap so that the closure plug 26 is visible. This preparation for the opening of the aluminum flange cap designated in the following as membrane 28 is typically carried out before the perforation with a cannula since the plastic flip-off cap has to be removed. To this extent sufficiently known constructions are referred to.

The inner or first part 12 furthermore comprises at a distance to the catch projections 20 an intermediate wall 30 running transversely to the longitudinal axis of the first part 12 as a second wall, which is also designated as a bottom wall, even if web-like sections of the circumferential wall 16 extend over the intermediate wall or bottom wall 30 in the direction of the second part 14, as the drawings illustrate. Furthermore, it can be seen from the drawings that the outside of the circumferential wall 16 comprises a serrated catch area 32 in order to serve as a catch for projections of the outer or second part 14 that are explained in the following.

Tongue-like lever elements 34, 36 and originate from the inner part 12 preferably uniformly distributed over the circumference of the circumferential wall 16 which elements are connected to the bottom wall 30 and can pivot about an axis running vertically to the longitudinal axis of the connector 10. Each lever element 34, 36—also called lever—therefore consists of a first or outer section 38 and a second or inner section 40, wherein in the base state, that is, when no radial forces are acting on the levers 34, 36, the outer section 38 projects section by section laterally over the outside surface of the circumferential wall 16, in contrast to which the inner section 14 projects with its hook-shaped end 42 section by section into the interior of the first part 12.

The outer or second part 14 also comprises a circumferential wall 44 forming a hollow cylindrical geometry and that is limited by a bottom wall 46 to be designated as the first wall, from which on the one hand a cannula 48 originates that extends in the longitudinal direction of the connector 10 in the direction of the first part and from which a so-called break-off connector 50 also originates running in the opposite direction which consists of plastic and into which the cannula 48 is adhered. The break-off connector 50 comprises a thin predetermined breaking point 52 for breaking off the tip 54 when the connector 10 starts being used. Refer to this extent also to known constructions.

Furthermore, it can also be seen from the drawings that the first wall or bottom wall 46 comprises a flange projecting over the circumferential wall 44 or comprises a flange-like handle so that a hat geometry basically results for the second part 14.

Tongue-like sections 56, 58 limited by slots are present in the circumferential wall 44 of the outer part 14, preferably also uniformly distributed over the circumference, that comprise hook-shaped projections on their free ends in order to be able to engage with the inner part 12. The projections 60 engage when the connection 10 is supplied into web-like sections 62, 64 present as recesses (catch receptacles) 66, 68 projecting over the second wall 30 and extending in prolongation of the circumferential wall 16. This ensures that the inner part 12 cannot be pulled out of the outer part 14 in order to loosen the parts 12, 14.

In the supplied state of the connector 10, as it can basically be seen in FIG. 1, the outer part 14 is supported on the outer sections 38 of the tongue-like lever elements 34. To this end the end sections of the outer sections 38 engage in corresponding recesses 70 in the circumferential wall 44 of the outer part 14 so that, observed in the axial direction, the upper limitations 72 of the recess 70 rest on the outer sections 38 of the lever elements 34, 36. At the same time the catch projections 16 of the tongue-like, pivotable section 56, 58 of the circumferential wall 44 of the outer part 14 engage into the catch receptacles 66, 68 of the web-like section 62, 64 of the inner part 12. In this position the distal end, that is, the tip 74 of the cannula 48, runs between the bottom wall 30 of the inner part 12 and the bottom wall 46 of the outer part 14 so that regardless of the fact that the bottom wall 30 has a perforation 76 in this area, there is no danger of injury for a user if his finger should unintentionally pass into the inner space of the inner bar 12 of the connector 14. In the representation in the drawings the distal end runs inside the bottom wall 30 of the inner part 12. To this extent this position of the invention is understood in such a manner and comprehended by the invention that the distal end is positioned between the bottom wall 30, 46 as the first wall and the second wall.

In FIG. 1 the connector 10 is set on the edge 12 in the supplied state in order to empty the vial 24. A relative movement than takes place between the vial 24 and the connector 10 without a relative movement taking place between the inner and the outer parts 12, 14, as a comparison of FIGS. 1 and 2 documents because the inner part 12 cannot be pushed into the outer part 14 since this is prevented by the lever elements 34, 36 since the latter support it with their outer sections 38 on the limitation of the recess 70, that is, on the wall 72.

FIG. 2 shows the position in which the connector 10 is located shortly in front of the unlocking. In this position the catch projections 20 of the tongue-like sections 18 of the circumferential wall 16 do not yet extend under the bottom 78 of the edge 22 of the vial 24.

In FIG. 3 the catch projections 20 snap under the flange-like edge 22 of the vial 24. At the same time the lever elements 34, 36 are pivoted since the projection 42 is guided along the circumferential surface of the edge 22 of the vial 224 with the result that a clockwise pivoting of the lever 34 shown on the left in the drawing takes place. In other words, the inside distance between the projection 42 of the lever 35 in the base position of the connector 10 (FIG. 1) to the central axis 80 of the connector 10 is less than one half the diameter of the edge 22 of the vial 24 with the result that the desired pivoting of the lever 34 is made possible by the interaction of the projection 42 with the circumferential surface of the edge 22. The vial 24 is pushed into the inner part 12 in accordance with the view of FIG. 4 until the membrane 28 of the closure of the vial 24 rests on the second wall, that is, bottom wall 30, as FIG. 4 illustrates. In this position the cannula 48 does not yet perforate the membrane 28. If the vial 24 with the inner part 12 is then pushed into the outer part 14, then the tip, that is, the distal end 74 of the cannula 48 penetrates the membrane 28 and its hole. At the same time the catch projection 60 of the tongue-like section 56, 58 of the circumferential wall 44 of the outer part 14 engages with the catch receptacles 66, 68 and slides along the circumferential surface of the circumferential wall 16 and can engage with the serrated projections 18. This has the advantage that if a tractive force would occur between the inner part 12 and the outer part 14 of the connector, the inner part 12 cannot be pulled out of the outer part 14 since the catch projections 66, 68 cooperate with the serrated projections 16 in the manner of barbs.

FIG. 5 shows the final state, that is, the cannula 48 has penetrated with its tip 74 into the vial 24 to the required extent. At the same time the catch projections 60 engage into catch recesses 82 in the circumferential wall 16 of the first part 12 so that a loosening between the inner and the outer parts 12, 14 is no longer possible. A radially outward bending away of the tongue-like sections 18 of the circumferential wall 16 is no longer possible in this position, as FIG. 5 shows, so that a loosening of the vial 24 is excluded. Furthermore, in the end position according to FIG. 5 the end area of the outer section 38 of the lever elements 34 engages into corresponding recesses 84 of the bottom wall 46 of the outer part 14. Therefore, the lever element 34 can be constructed to be relatively long without this resulting in disadvantages in the construction height and therefore in the compactness of the connector 10.

The exemplary embodiments of FIGS. 6 and 7 differ from those of FIGS. 1 to 5 in that elements consisting in particular of an elastomeric material and in the shape of a membrane 86 shaped like a hat (FIG. 7) or of a plug 88 (FIG. 6) originate from the bottom wall 30, that is, the second wall, which elements are penetrated by the cannula 48, that is, its tip 74 before the penetration of the membrane 28 of the closure of the vial 24, wherein the elements 86, 88 are placed on the one hand tightly around the cannula 48 and on the other hand make a sealing against the membrane 28 possible with the result that during the penetration of the membrane 28 contents of the vial 29 cannot penetrate outward. This is especially advantageous if toxic substances are present in the vial 24.

Another preferred embodiment of a connector 100 can be seen in FIGS. 8 to 15. Refer to the previously described features and explanations for the construction and functioning of the connector 100, in particular regarding the possibility of adjusting the inner or first part 12 to the second or outer part 14 only if the inner part 12 is engaged on the vial 24, that is, on its edge 22. Also, basically the same reference numerals are used for the same elements.

In distinction to the embodiment of FIGS. 1 to 7, an adjustment of the first part 12 to the second part 14 does not take place by an axial shifting toward one another but rather by a rotational movement of the first part 12 to the second part 14. This also produces a telescopic adjusting of the first part 12 to the second part 14 along the longitudinal axis 118 of the connector 100 in order that the tip 54 of the cannula 48 can penetrate the membrane 28. At the same time it is ensured that a rotation of the first and second parts 12, 14 is possible only in one direction, namely, in the direction of penetration. An opposite rotation is prevented so that the same security results as was presented in conjunction with the previously explained exemplary embodiments. This also applies to the function of the lever elements 34, 36, that originate from the inner or first part 12 and prevent a rotation of the second part 14 to the first part 12 until the first part 12 has engaged onto the closure plug 26 of the vial 24.

In order to make possible an axial adjustment of the inner part 12, that is, of the vial holder, to the outer part 14, the cannula holder, according to the exemplary embodiment of FIGS. 8 to 16 a rotational movement between the inner part 12 and the outer part 14 is carried out. To this end the inner part 12 has a helical contour 102 that originates from the circumferential wall 16 of the inner part 12 and therefore projects over its outer circumferential surface 116. The helical contour 102, which can have a strip-shaped course, therefore forms a screw thread or a section of one, such as also results in particular from FIG. 11. This contour 102 is interrupted in the area of the slots that limit the sections 18 and the lever elements 34, 36. This is also clear from FIG. 11. Instead of one screw thread, several screw threads can also be provided.

The contour 102 running coaxially to the longitudinal axis 118 of the vial holder comprises a serrated structure in order to cooperate in an engaging manner with a tongue-like element 120 that is free-cut in the circumferential wall 44 of the outer part 14 and comprises one or more projections 122 extending in the direction of the contour 102 which projection or projections cooperate with the serrated profiling of the contour 102 in such a manner that in the exemplary embodiment the outer part 14 can be rotated exclusively clockwise, as a result of which the cannula 48 is adjusted in the direction of the closure plug 26 in order to be able to perforate its membrane 28. A counterclockwise rotation is not possible since in this case the hook-shaped projection 122 engages with corresponding, geometrically aligned projections of the serrated profiling of the contour 102.

As also results from the sectional views of FIGS. 8 to 10, the contour 102 following the screw thread for a section of such a screw thread runs inside an adapted recess 124 in the circumferential wall 44 of the outer part 14 that therefore forms a guide during the rotational movement.

Of course, the contour can also originate from the second part and the element from the first part. Such a construction is also comprised by the invention.

As results in particular from FIG. 12, diametrically opposed, wing-shaped elements 130, 132 project from the vial-side edge of the circumferential wall 16 of the inner part 12 that serve as a handle in order to fix the first one on the vial 24 or on the closure plug 26 during the engagement of the inner part 12 on the closure plug 26 in order that the desired relative rotational movement between the inner part 12 and the outer part 14 is made possible. In order to facilitate the rotation of the outer part 14 to the inner part 12 a handle 136 projects radially from the circumferential wall 44 of the outer part 14.

A comparison between the FIGS. 8 to 10 illustrates that the cannula 48 is adjusted in the direction of the closure plug 24 as a function of the rotational position of the outer part 14 to the inner part 12. The position is shown in FIG. 8, in which the outer sections 38 of the lever elements 34, 36 are pivoted inward so that a rotation of the outer part 14 to the inner part 12 becomes possible. In other words, the initial position is shown in which a rotation of the outer part 14 to the inner part 12 can take place in order to be able to adjust the cannula axially 48 in the direction of the membrane. In FIG. 9 the outer part 14 was adjusted opposite the inner part 12 so that the membrane 28 has already been perforated by the tip 54 of the cannula 48. FIG. 10 reflects the final position in which the cannula 44 has penetrated the membrane 28 to the desired extent. At the same time a locking of the outer part 14 with the first part 12 is possible in this position.

FIGS. 16 to 20 show another embodiment of a transfer device 200 to be emphasized that belongs to the teaching of the invention. Therefore, basically the same reference numerals according to the FIGS. 1 to 15 are used for the same elements.

The transfer device designated below as connector 200 consequently consists of the inner or first part 12 and the outer or second part 14 that can be axially shifted to one another. In order to ensure that if the connector 200 does not surround the edge of the bottle (vial 24) in the proper manner, that is, the inner or first part 12 does not extend behind the bottom 78 of the edge 22 of the vial 24, an axial shifting between the first part 12 and the second part 14 and therefore a penetration of the tip 74 of the cannula 48 through the opening 76 in the second wall 30 of the first store inner part 12 does not take place, the second or outer part 14 comprises several tongue-shaped, elastic elements 202, 204 that are limited by slots, are preferably uniformly distributed over the circumference and are designated in the following as tongues. The tongues 202, 204 comprise catch projections 206, 208 extending inward at their ends, that is, in the direction of the central axis 80 of the connector 200 and that can have a wedge-shaped or ramp-shaped geometry. In order to prevent an axial adjustment of the inner part 12 to the outer part 14 in the case of an improper fixing of the connector 20 to the vial 24, the catch projections 206, 208 extend into corresponding recesses 210, 212 in the circumferential wall of the inner part 12. When the outer part 14 is loaded with pressure in the direction of the inner part 12 the catch projections 206, 208 lie with their free outer surfaces 214, 216 running vertically to the axis 80 on lower edges 218, 220 of the recesses 210, 212, which prevents an axial adjusting of the first and second parts 12, 14 to one another. This ensures that the tip 74 of the cannula 48 remains in the intermediate space between the second wall 30, also designated as an intermediate wall, of the first part 12 and between the outer limiting wall or first wall 46 of the second part 14 and therefore the danger of injury is excluded. If the connector 200 is pushed onto the vial 24, the catch projections 206, 208 remain in the recesses 201, 212 of the inner part 12 until the inwardly directed projections 20 of the first part 12 extend behind the lower edge of the flange-like edge 22 of the vial 24. The same applies if instead of the flange-like edge 22 another element that makes a fixing of the connector 200 possible is extended behind.

FIG. 17 shows a position in which the first part 12 extends with the free edge of the inwardly extending projections 20 behind the bottom of the edge 22 of the vial 24 of a closure surrounding the vial 24. As a consequence of this, the catch projections 206, 208 with the elastic tongue-elements 202, 204 are bent outward by cooperating with the top or the upper corner of the edge 22, as FIG. 18 illustrates.

In order to ensure this, the distance between the recesses 210, 212 to the catch projections 20 of the first part 122 that extend behind the bottom of the vial edge 22 are selected in such a manner that upon a proper fixing of the first part 12 on the vial 24 the catch projections 206, 208 of the second part 14 can slide along the circumferential upper edge of the flange-like edge 22 if a force acts on the second part 14 in the direction of the first part 12. The catch projections 206, 208 therefore come in engagement with the catch recesses 210, 212 to such an extent that an axial adjustment of the first part 12 to the second part 14 is no longer prevented and therefore the cannula 48 with its tip 74 can be adjusted in the direction of the closure plug 26 and therefore of the membrane 28, closing the latter in order to be able to perforate them during a further axial shifting of the first part 12 to the second part 14. The beginning of the penetration can be recognized in FIG. 19. If a further shifting of the inner part 12 to the outer part 14 takes place, the catch projections 206, 208 are shifted along the outside of the first part 12 until the catch projections 206, 208 extend behind the bottom edge of the first part 12 on account of the elastic properties of the tongue elements 202, 204, as can be gathered from FIG. 20, in which the vial 24 is not sketched in.

Therefore, the connector 200 fulfills the requirement that the cannula 48 with its tip 76 is not freely accessible in the non-used state and in the case of an improper surrounding of the vial 24, and therefore the danger of an injury is extruded. Only when the first part 12 properly surrounds the closure area of the vial 24 is there an unlocking and therefore an activation of the connector 200 in such a manner that an axial adjustment between the first part 12 and the second part 14 is made possible and therefore the cannula 48 can be adjusted in the direction of the membrane 28 of the closure plug 26 for penetrating them, as can be seen in a reconstructable manner from the FIGS. 16 to 20 that are self-explanatory to this extent.

Furthermore, it should be noted that in the case of the exemplary embodiment of FIGS. 16 to 20—as in the previous ones—there is also the constructive possibility that the second part 14 is locked in such a manner during the axial shifting to the first part 12 that a drawing a part, that is, an adjustment of the first part 12 to the second part 14 counter to the direction of penetration of the cannula 48 is not possible.

LIST OF REFERENCE NUMERALS 10 connector, transfer device
12 first (inner part)
14 second (outer) part
16 circumferential wall of 12
18 section
20 projections
22 edge
24 vial, bottle
26 closure plug
28 membrane
30 second wall
32 catch area
34 lever element
36 lever element
38 outer section
40 inner section
42 end
44 circumferential wall of 14
46 first wall
48 cannula 50 break-off connector
52 predetermined breaking point
54 tip
56 section
58 section
60 projection
62 section
64 section
66 recess
68 recess
70 recess
72 limitations
74 tip
76 perforation
78 bottom
80 central axis
82 catch recesses
84 recess
86 membrane
88 plug
100 connector, transfer device
102 contour
116 outer circumferential surface
118 longitudinal axis
120 element
122 projection
124 recess
130 wing
132 wing
136 handle
200 connector, transfer device
202 tongue
204 tongue
206 catch projection
208 catch projection
210 recess
212 recess
214 outer surface
216 outer surface
218 lower edge
220 lower edge

The invention claimed is:

1. A transfer device for tapping or delivering a fluid from a bottle closed by a closure, comprising:

a hollow cylindrical first part that can be set on the bottle, surrounds the closure, and comprises a first circumferential wall, a hollow cylindrical second part that can be adjusted relative to the first part and with a first wall running transversely to a longitudinal axial direction of the second part, a puncturing needle starting from the first wall and extending in the direction of the first part for making it possible to pierce the closure, wherein, if there is no surrounding of the closure by the first part, the first part cannot be adjusted axially relative to the second part, and, in the case of the first part surrounding the closure, the first part can be adjusted relative to the second part for piercing the closure, wherein the first part comprises a second wall running transversely to a longitudinal axis of the first part, and that if the first part and the second part cannot be adjusted axially relative to one another, the distal end of the puncturing needle runs between the first wall and the second wall, and either:

at least one lever element originates from the circumferential wall of the first part with a first section extending in the direction of the second part, and with a second section extending in the direction of the opening of the first part, which opening faces the bottle, wherein given the lack of adjustability between the first part and the second part to one another, the first section projects laterally outward over the circumferential wall of the first part and the second section extends into the inside of the first part, the first section cooperates with the second part to prevent a shifting of the first part to the second part and, in the case of the first part surrounding the closure of the bottle, the second section of the at least one lever element is shifted radially outward with a simultaneous disengagement of the first section with the second part;

or the second part comprises tongue-shaped elements limited by slots running in the longitudinal direction of the second part, and with projections projecting into the interior of the second part, that the projections engage into recesses in the first part upon the lack of axial adjustability between the first part and the second part, which recesses have a distance to a lower edge of the first part such that when the first part surrounds the bottle in a locked manner, the projections disengage with the recesses by interacting with the bottle, and when the puncturing needle penetrates the closure, the projections engage behind the lower edge of the first part which has a form of a flange;

or in order to rotate the first part to the second part, one of the parts comprises a helically running contour along the first circumferential wall, or a circumferential wall of the second part, and around the longitudinal axis of the transfer device, wherein the contour interacts with an element originating from the other part;

wherein the contour has a serrated profile and the element comprises a projection that interacts with the contour, wherein an interaction takes place in such a manner that a rotation of the first part to the second part takes place exclusively in the direction of penetration of the puncturing needle.

2. The transfer device according to claim 1, wherein the first part can be adjusted relative to the second part by an axial adjusting, or a telescopic rotating.

3. The transfer device according to claim 1, wherein the second wall is configured to be perforated in an axial prolongation of the puncturing needle.

4. The transfer device according to claim 1, wherein the first part and the second part are locked to one another in the case of a lack of adjustability between the first part and the second part, wherein projections projecting from the inside of a circumferential wall of the second part engage in recesses of the circumferential wall of the first part.

5. The transfer device according to claim 4, wherein the first circumferential wall of the first part comprises recesses spaced in the axial direction to each other for a gradual locking of the projections.

6. The transfer device according to claim 1, wherein an opening-side edge of the first part comprises inwardly projecting projections for extending behind a flange-like edge surrounding an opening of the bottle, wherein the first part is configured to prevent a disengagement between the first section of the at least one lever element and the second part before the first part extends behind the flange-like edge.

7. The transfer device according to claim 1, wherein the first part is configured to be shifted into the second part by loading the second wall with pressure.

8. The transfer device according to claim 3, wherein a membrane, or a plug, originates from the second wall, and runs in the axial prolongation of the puncturing needle, sealing the puncturing needle on its circumference during a perforation.

9. The transfer device according to claim 1, wherein, in order to fix the first part on the bottle, a handle projects from the first part.

10. The transfer device according to claim 1, wherein the projections are constructed in a form of ramps, or wedges, in their free areas in such a manner that a surface running obliquely to the longitudinal direction of the transfer device slides along an edge of the bottle.

11. The transfer device according to claim 1, wherein the first part engages with the second part during an axial shifting in such a manner that a shifting counter to the direction of penetration of the puncturing needle is prevented.

12. The transfer device according to claim 1, wherein, during a shifting of the second part in the direction of penetration of the puncturing needle, the first part interacts with the second part in such a manner that a shifting of the second part to the first part counter to the direction of penetration is prevented.

13. The transfer device according to claim 1, wherein the at least one lever element that originates from the circumferential wall of the first part is a tongue-like lever element.

14. The transfer device according to claim 1, wherein the element that originates from the other part is a tongue-like element.

15. The transfer device according to claim 1, wherein the element that originates from the other part originates from a circumferential wall of the other part.

16. The transfer device according to claim 1, wherein the projection is a hook.

17. The transfer device according to claim 9, wherein the handle is in a form of two wings projecting radially from the first part.

18. The transfer device according to claim 1, wherein, in order to rotate the first part to the second part, the element originates from a circumferential wall of the other part.

19. The transfer device according to claim 1, wherein, in order to rotate the first part to the second part, the contour interacts with a tongue originating from the other part.

20. The transfer device according to claim 1, wherein the contour projects over an outer circumferential surface of the circumferential wall of the first part, and wherein an inner circumferential surface of the second part comprises at least one recess adapted to the course of the contour, at least in sections in which recess the contour is guided.

* * * * *